(12) United States Patent
Stein

(10) Patent No.: US 8,888,568 B2
(45) Date of Patent: Nov. 18, 2014

(54) THREAD INSPECTION AND POLISHING DEVICE

(76) Inventor: Ronald B. Stein, Wallingford, PA (US)

( * ) Notice: Subject to any disclaimer, the term of this patent is extended or adjusted under 35 U.S.C. 154(b) by 799 days.

(21) Appl. No.: 12/924,932

(22) Filed: Oct. 8, 2010

(65) Prior Publication Data

US 2011/0086581 A1    Apr. 14, 2011

Related U.S. Application Data

(60) Provisional application No. 61/278,959, filed on Oct. 14, 2009.

(51) Int. Cl.
  *B24D 15/00*    (2006.01)
(52) U.S. Cl.
  USPC ........... 451/513; 451/524; 451/527; 451/552; 451/557
(58) Field of Classification Search
  USPC ............. 451/48, 59, 513, 523, 524, 525, 527, 451/530, 552, 557
  See application file for complete search history.

(56) References Cited

U.S. PATENT DOCUMENTS

| | | | | |
|---|---|---|---|---|
| 2,046,240 A * | 6/1936 | Bayley | ........................... | 451/531 |
| 2,311,060 A * | 2/1943 | Lurrain | ........................ | 451/524 |
| 3,557,496 A * | 1/1971 | Martin | ......................... | 451/533 |
| 3,775,923 A * | 12/1973 | Martin | ......................... | 451/524 |
| 4,014,062 A * | 3/1977 | Scott et al. | .................. | 15/104.04 |
| 4,016,938 A * | 4/1977 | Rice | ................................. | 173/1 |
| 4,077,808 A * | 3/1978 | Church et al. | .................. | 501/80 |
| 4,403,363 A * | 9/1983 | Hess | ........................... | 15/104.04 |
| 4,644,394 A * | 2/1987 | Reeves | .......................... | 348/131 |
| 4,988,325 A * | 1/1991 | Alderson et al. | .............. | 446/397 |
| 5,043,377 A * | 8/1991 | Nogi et al. | ..................... | 524/437 |
| 5,157,802 A * | 10/1992 | Guidry et al. | ..................... | 15/88 |
| 5,309,490 A * | 5/1994 | Bayersten | ..................... | 376/310 |
| 5,366,524 A * | 11/1994 | Holcombe et al. | .............. | 51/293 |
| 5,568,263 A * | 10/1996 | Hanna | .......................... | 356/638 |
| 5,932,789 A * | 8/1999 | Stein | ................................. | 73/7 |
| 7,077,737 B2 * | 7/2006 | Manigel | ........................ | 451/533 |
| 8,662,962 B2 * | 3/2014 | Petersen | ......................... | 451/59 |
| 2009/0325470 A1 * | 12/2009 | Petersen | ......................... | 451/59 |

* cited by examiner

*Primary Examiner* — Eileen P. Morgan
(74) *Attorney, Agent, or Firm* — Panitch Schwarze Belisario & Nadel LLP

(57) ABSTRACT

A system and method providing improved capability for inspecting and repairing threads of bolts and threaded holes is disclosed. Polishing stones comprised of epoxy and metallic oxide are used in conjunction with dye to identify threads in need of repair and make them visible to a maintenance worker.

13 Claims, 19 Drawing Sheets

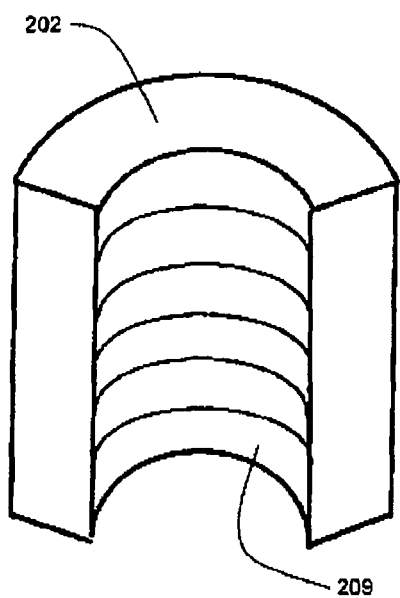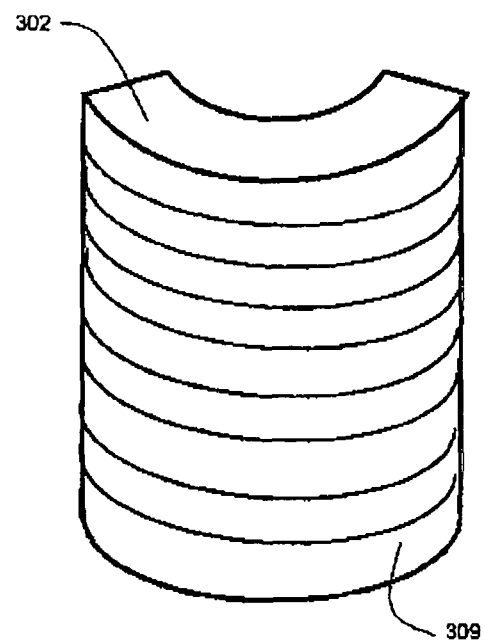
FIG. 2B
FIG. 2C

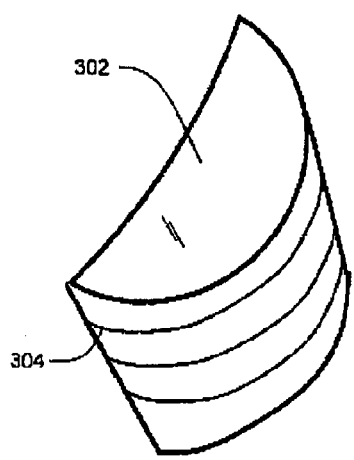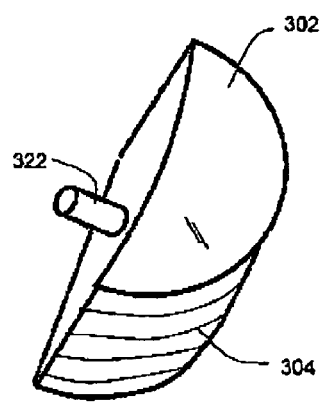
FIG. 3A
FIG. 3B

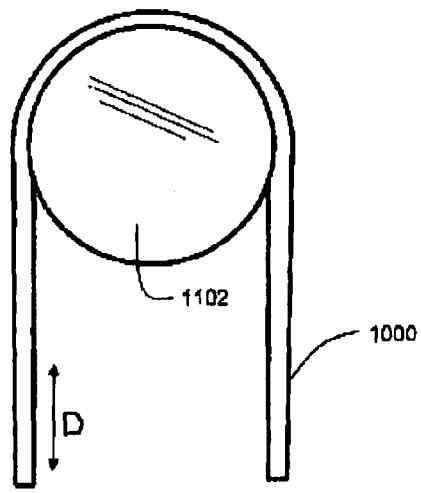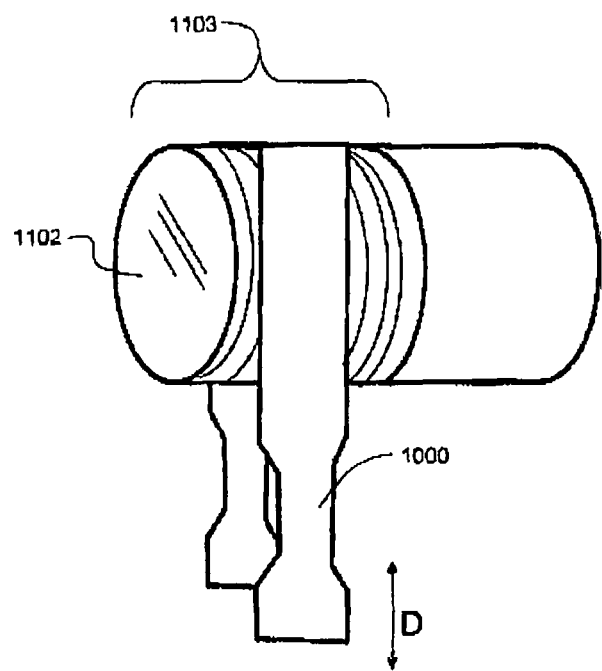
FIG. 11A
FIG. 11B

THREAD INSPECTION AND POLISHING DEVICE

CROSS-REFERENCE TO RELATED APPLICATIONS

This application claims benefit to U.S. Provisional Patent Application No. 61/278,959, filed Oct. 14, 2009.

FIELD OF THE INVENTION

The present invention relates to maintenance and repair of threaded bolts and threaded holes. More particularly, the present invention relates to a method and apparatus for inspecting and repairing large-sized bolts and threaded holes.

BACKGROUND

U.S. Pat. No. 5,932,789, to Stein is incorporated herein by reference, and is hereinafter referred to as the '789 patent. The '789 patent discloses a bolt thread inspection and thread polishing device. The '789 patent provides a variety of advantages, such as the ability to quickly identify damaged areas of bolts, and also provides a method of repairing the identified damage. However, there is an ongoing need to improve maintenance of bolts and threaded receptacles in large-size, critical situations, such as large power generators, boilers, and ship propulsion systems, to name a few.

SUMMARY OF THE INVENTION

While the device disclosed in U.S. Pat. No. 5,932,789 provided an efficient way to detect damage to large bolts, there were various shortcomings of that device. In particular, the '789 device did not provide inspection or repair capabilities for threaded holes. Another drawback of the '789 device is that in certain conditions, the use of the device may adversely affect the threads. These issues are addressed in embodiments of the present invention. These advantages, and others, are disclosed in the detail description that follows.

BRIEF DESCRIPTION OF THE DRAWINGS

FIG. 2B shows a perspective view of a concave polishing stone.

FIG. 2C shows a perspective view of a convex polishing stone.

FIGS. 3A and 3B show a convex polishing stone.

FIG. 11A and FIG. 11B show use of the embodiment of FIG. 10B.

DETAILED DESCRIPTION

Embodiments of the present invention provide improved capability for inspecting and repairing threads of bolts and threaded holes. More particularly, embodiments of the present invention are well suited for large bolts, typically found in heavy industry such as power plants, large ships, and the like. The threads on these bolts may be damaged during the course of periodic maintenance. In some cases, these bolts have a diameter of over 4 inches, and may cost over $10,000 per bolt, and therefore, repair is often preferable to replacement. In addition to bolt threads, repair and inspection is also needed for threaded holes, such as nuts or tapped bolt holes in machinery.

Figure 1:
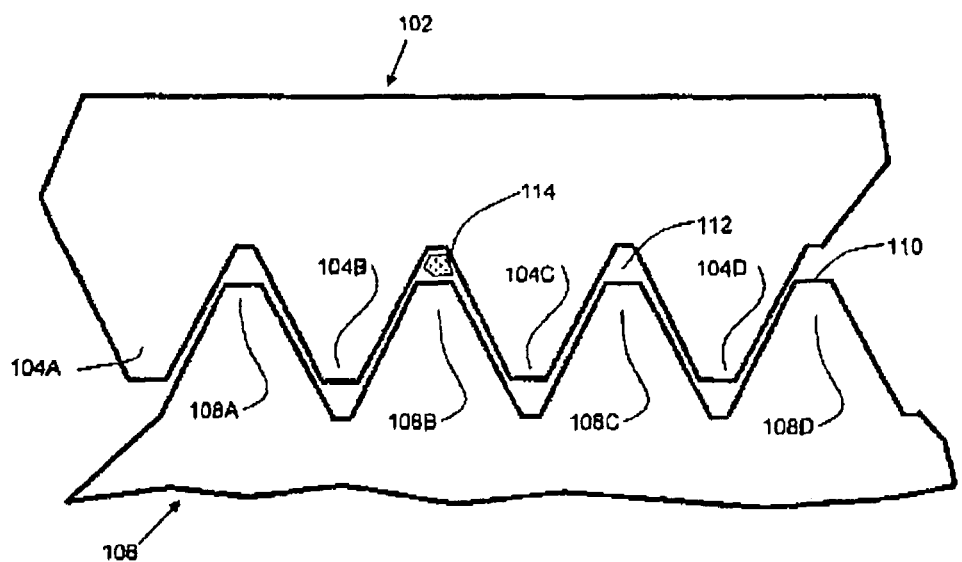
FIG. 1 shows thread details of a prior art concave polishing stone.

FIG. 1 shows thread details of a prior art concave polishing stone 102, similar to that shown in FIG. 2B of the '789 patent. Polishing stone 102 has a plurality of threads 104A-104D that engage corresponding threads 108A-108D of bolt 106. Each thread has a peak (shown generally as 110). As the polishing stone 102 is moved over the threads of the bolt 106, small metal fragments 114 from the bolt may form in the void (generally referred to as 112) between the thread peaks 110 and the polishing stone 102. These metal fragments can wear the bolt threads, causing damage to threads of bolt 106. Polishing stone 102 has a spacing factor of 1, meaning that there is a polishing stone thread for every bolt thread. In one embodiment, the polishing stone 102 is formed from a mixture of epoxy and aluminum oxide. In one embodiment, polishing stone 102 has a shape of a 120 degree arc, with internal threads to line up with the threads on a bolt of similar diameter to the inner surface of polishing stone 102.

Figure 2:
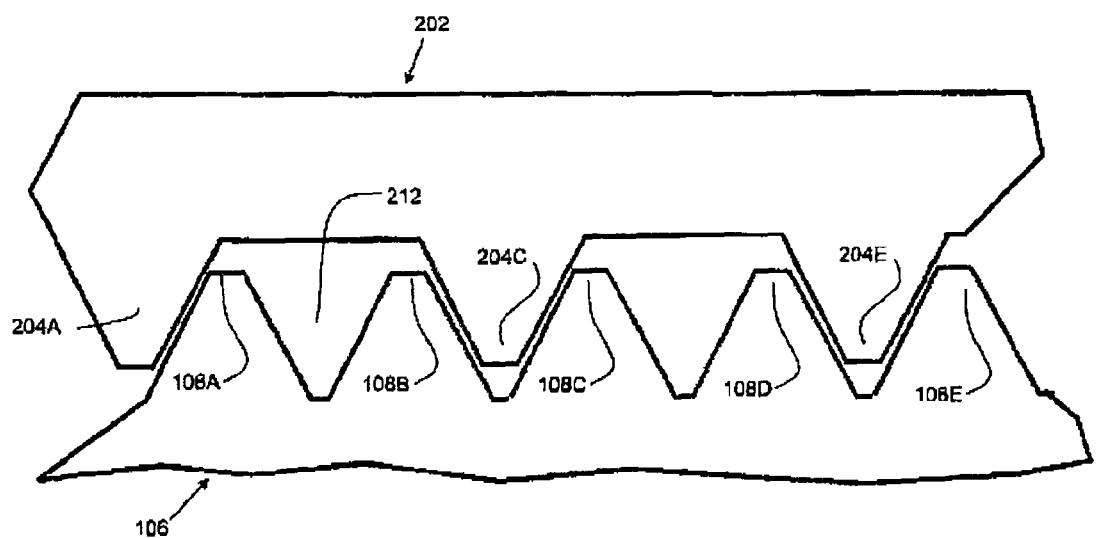
FIG. 2 shows thread details of a concave polishing stone in accordance with an embodiment of the present invention.

FIG. 2 shows thread details of a polishing stone 202 in accordance with an embodiment of the present invention. Polishing stone 202 has a plurality of threads 204A, 204C, and 204E that engage threads of bolt 106. Polishing stone 202 has threads spaced at wider intervals than the prior art polishing stone 102. In FIG. 2, a polishing stone with a spacing factor of 2 is shown, meaning that there is a polishing stone thread for every two bolt threads. For example, thread 108A and 108B are bounded by thread 204A and 204C of polishing stone 202. By using a spacing factor of 2 or more, a large void 212 is formed between the threads of the bolt 106, and the polishing stone 202. Large void 212 provides an escape path for metal fragments, so that they do not wear the peaks (see 110 of FIG. 1) of the threads of bolt 106. Note that while a spacing factor of 2 is illustrated in FIG. 2, larger spacing factors are contemplated, and within the scope of the present invention.

FIG. 2B shows a perspective view of a concave polishing stone 202, and FIG. 2C shows a perspective view of a convex polishing stone 302. In general, polishing stones 202 and 302 are arc-shaped, having threads on at least one side, either the inner side 209 or the outer side 309. In one embodiment, both sides 209 and 309 of the polishing stone may be threaded, providing a polishing stone capable of polishing both a bolt and a threaded hole, such as a nut.

FIGS. 3A and 3B show perspective views of a convex polishing stone 302. Convex polishing stone 302 is intended for threads inside a nut or stud hole. FIG. 3A shows a front perspective view of convex polishing stone 302, having threads (shown generally as 304). The convex polishing stone 302 has a spacing factor of 2 or greater.

Figure 4:
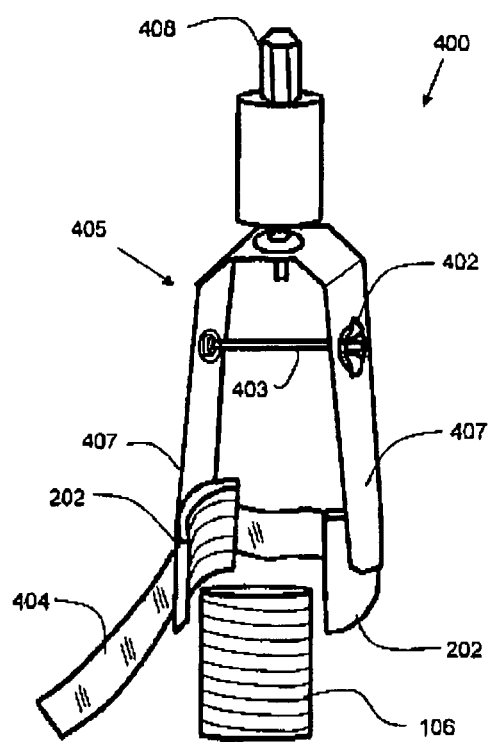
FIG. 4 shows an improved polishing stone holder.

FIG. 4 shows an improved polishing stone holder 400. U-shaped metal frame 405 has polishing stones 202 attached at the distal ends of each frame leg 407. Wing nut 402 engages threaded bolt 403 to provide for adjusting the pressure that polishing stones 202 exert on bolt 106. Strap 404 is used to provide additional security by being wrapped around the polishing stones 202 snug against bolt 106. Strap 404 is intended to wrap around the outside of frame legs 407 to keep the polishing stones 202 centered. In one embodiment, strap 404 comprises a fastener such as a hook-and-loop fastener or snaps to secure the strap 404 around the polishing stones 202. One end of the strap 404 may be permanently secured to a frame leg 407 via adhesive or another fastening means, such as a grommet. Drive nut 408 engages a ratchet (not shown) or drill (not shown) to turn the stone holder 400. If a drill is used, a slow speed setting is preferable, to avoid damage to the bolt 106.

Figure 5:
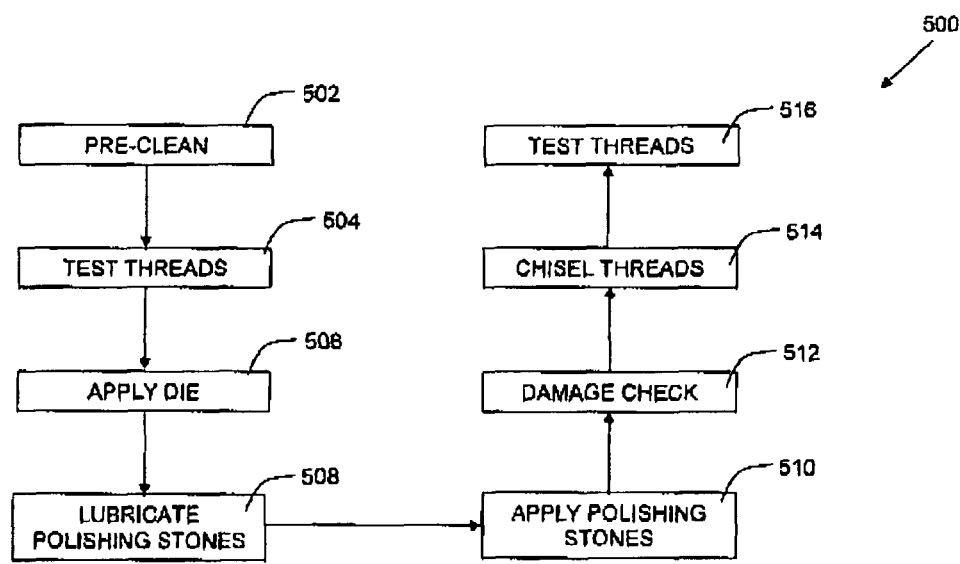
FIG. 5 shows a flowchart indicating process steps to inspect and repair threads.

FIG. 5 shows a flowchart 500 indicating process steps to inspect and repair threads. In process step 502, the workpiece ("workpiece" refers to a bolt or threaded hole) is pre-cleaned prior to inspecting the threads. In one embodiment, the step of pre-cleaning is performed via absorbent pads soaked with rubbing alcohol. This step cleans the threads, and removes any major deposits of grime and grit that may be present on the workpiece. In process step 504, the threads are given a first test. For a bolt, this comprises slowly putting a corresponding nut on the bolt and feeling for any areas where the nut does not turn freely, which may be indicative of an issue with the threads. If the workpiece is a threaded hole, then a bolt is used to test the threads. Next, a layout die is applied to the workpiece in step 506. In step 508, the polishing stones are lubricated with rubbing alcohol to facilitate smooth motion when the polishing stones are applied to the workpiece. In process step 510, the polishing stones are applied to the workpiece. This step may be performed by hand initially, and then subsequently, performed via a stone holder such as 400 of FIG. 4. The stone holder allows the polishing stones to be applied to the workpiece via a ratchet or drill. When a drill is used, it is preferable to use a slow speed to avoid damage to the workpiece. In step 512 the workpiece is checked for damage. Any areas with notable thread damage are indicated by an absence of layout die. In the case of a threaded hole, an inspection mirror may be used to view the threads if direct viewing is not feasible. In step 514, damaged areas are repaired by chiseling at an approximate 90 degree angle to the X axis of the bolt (see FIG. 8A and corresponding description). In step 516, the threads are tested again, similar to step 504, to confirm that the thread damage has been fixed. At this point, a nut should move smoothly when engaged with a repaired bolt. If there are still some places where the nut does not turn freely around the repaired bolt, process steps 506-514 may be repeated until the workpiece is repaired, and the nut turns smoothly on the bolt.

Figure 6:
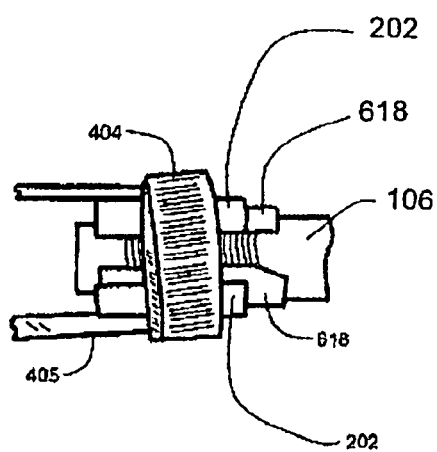
FIG. 6 shows the method step of pre-cleaning.

FIG. 6 shows the method step of pre-cleaning. Absorbent pads 618 are soaked in a fast-evaporating solvent, such as rubbing alcohol, and then inserted in front of polishing stones 202. Strap 404 is then wrapped around workpiece 106, and the polishing stone holder is rotated around the workpiece (bolt) 106 to clean it in preparation for inspection and repair.

Figure 7:
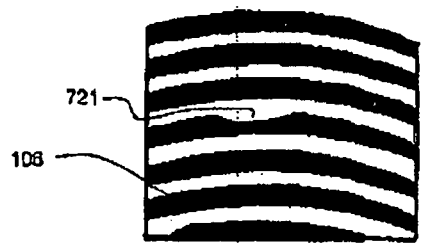
FIG. 7 shows an indication of thread damage.

FIG. 7 shows an indication of thread damage on bolt 106. A damaged thread is indicated generally by reference 721. Since the thread 721 was out of alignment, the polishing stone removed the dye from that area, making the defect immediately visible to a maintenance worker.

Figure 8A:
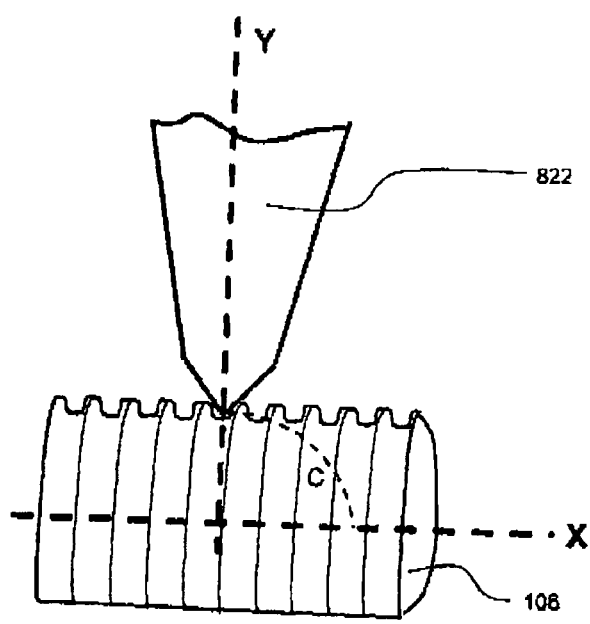
FIGS. 8A and 8B show instances of repairing threads.

FIG. 8A shows an instance of repairing threads in a bolt 106. Chisel point 822 is oriented at angle C with respect to axis X of the bolt 106. Angle C is preferably about 90 degrees, so that the chisel point is aligned with an imaginary Y axis that is perpendicular to the X axis of the bolt. The chisel is then struck with a mallet (not shown) to move the threads back to their proper position, without excess metal loss that occurs with sanding, or with taps and dies.

Figure 8B:
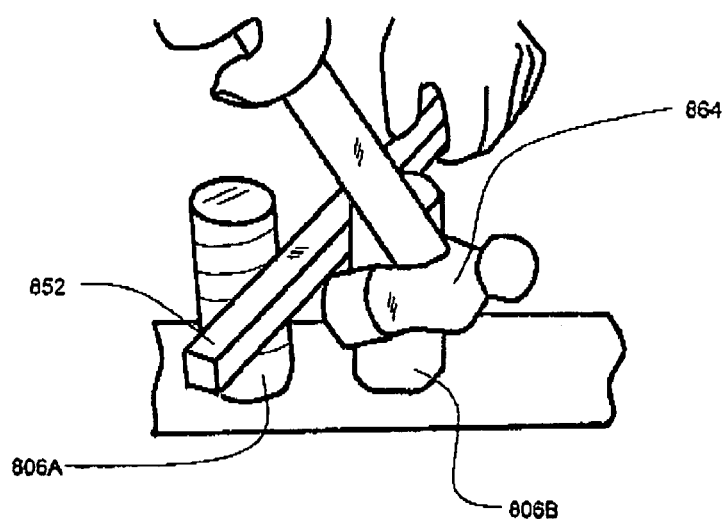

FIG. 8B shows an instance of repairing bolt threads with limited working space. In this case, bolt 806A is undergoing repair. However, since bolt 806A is in close proximity to bolt 806B, using a conventional chisel is not feasible. Therefore, a special bar chisel 852 has been designed for this purpose. Chisel 852 has a blade that is applied to bolt 806A and then struck with mallet 864 to make the repairs. In this way, bolt threads can be repaired, even in tight spaces.

Figure 8C:
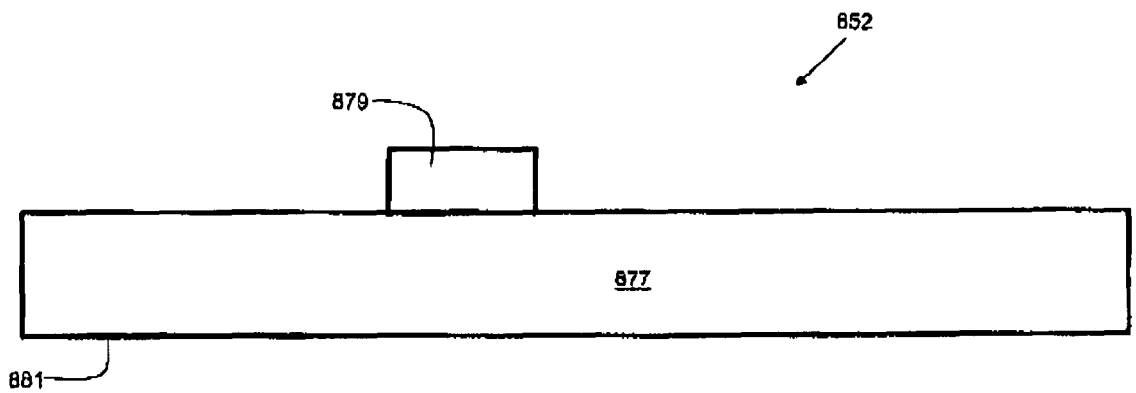
FIG. 8C shows a side view of a chisel.

FIG. 8C shows a side view of chisel 852. Chisel 852 is comprised of bar 877, and chisel point 879. During use to repair a bolt thread, chisel point 879 is applied to a bolt, and then a mallet is used to strike bar 877 on the opposite side, (e.g. at point 881) to repair the bolt threads.

Figure 9:
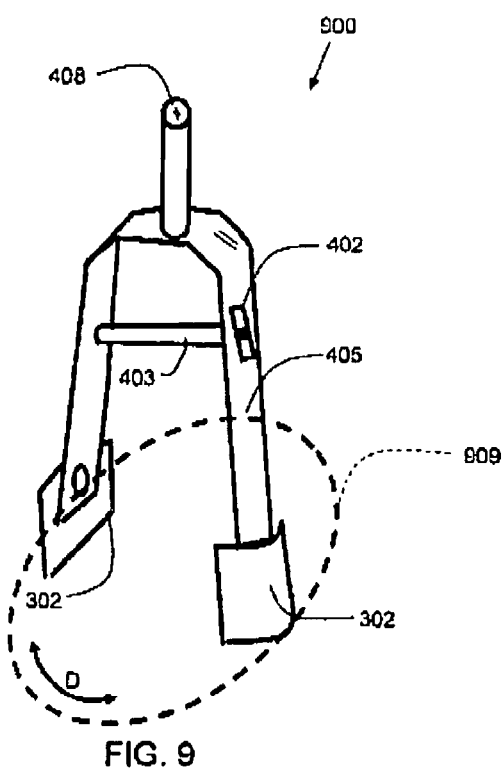
FIG. 9 shows a polishing stone holder as used with convex polishing stones.

FIG. 9 shows a polishing stone holder 900 as used with convex polishing stones 302. Polishing stone holder 900 is similar to polishing stone holder 400 of FIG. 4, with the exception of the polishing stones 302 which are fastened to the outer surface of U-shaped metal frame 405, so they can contact the inner diameter of a threaded hole (indicated as 909). The polishing stone holder is then turned back and forth along path D, so that the polishing stones 302 engage the threads of a threaded hole such as a nut or bolt hole within a piece of machinery.

Figure 10A:
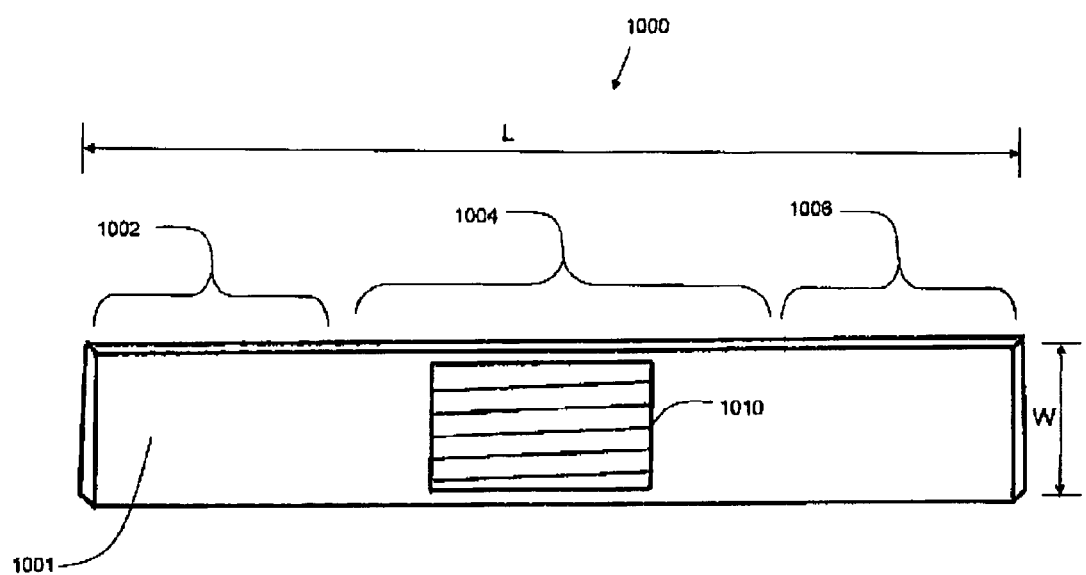
FIGS. 10A-10C show alternative embodiments of the present invention.

FIG. 10A shows an alternate embodiment of the present invention, a flexible polishing stone holder 1000. Flexible polishing stone holder 1000 comprises a strap 1001. Strap 1001 is elongated, preferably having a length at least four times its width. Depending on the application, the width W of strap 1001 is preferably in the range of 2 inches to 4 inches, and the strap length L is in the range of 8 inches to 10 inches. In one embodiment, strap 1001 is comprised of a urethane that us flexible after curing. The strap 1001 may also be comprised of rubber, canvas, or other sturdy textile. Strap 1001 comprises two end portions 1002 and 1006, and middle portion 1004. Affixed to the middle portion is polishing stone 1010. In one embodiment, polishing stone 1010 is square or rectangular, and may be comprised of an epoxy casting with aluminum oxide mixed into the epoxy. In one embodiment, polishing stone 1010 is cast as part of strap 1010, with the thread pattern as part of a mold (not shown) used to form the strap 1001. In this case, the polishing stone 1010 and polishing stone holder (strap 1001) are comprised of a single piece of cast urethane material.

Figure 10B:
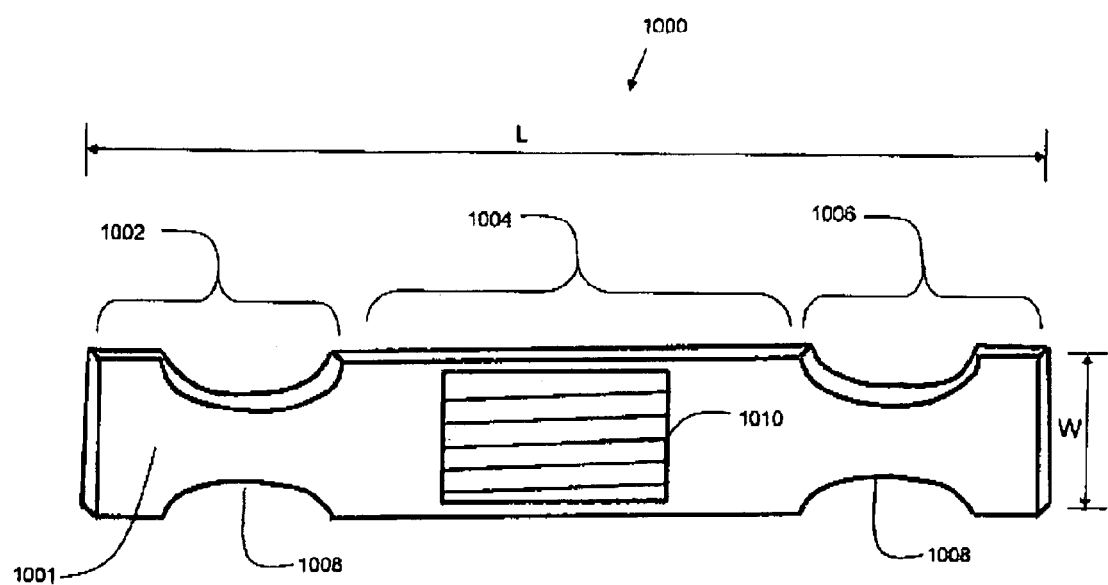
Figure 10C:
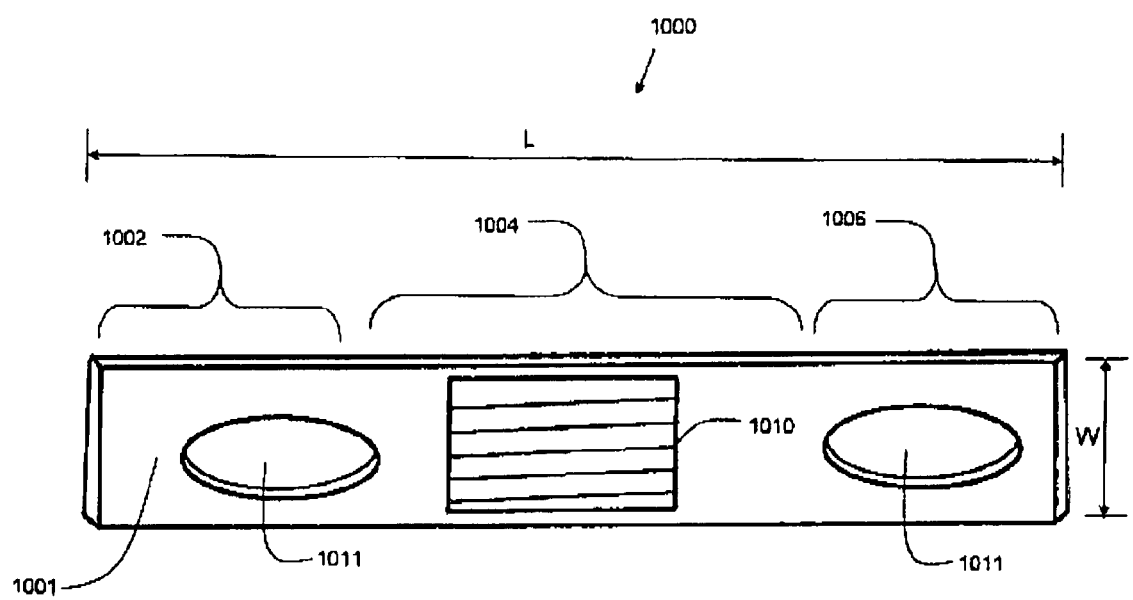

In an alternative embodiment, polishing stone 1010 is a thin piece of urethane mixed with a metal oxide that is affixed to strap 1001 via an adhesive (e.g. epoxy or glue). In one embodiment, polishing stone 1010 has a spacing index of 2. As shown in FIG. 10B, end portions 1002 and 1006 may further comprise cutout areas 1008 disposed within end portions 1002 and 1006. Note, for illustrative clarity, not all of the cutouts shown in FIG. 10B are labeled with a reference number. The cutout areas facilitate a user gripping the end portions to polish threads of a bolt in a manner similar to that described previously. An advantage of the embodiment utilizing a flexible stone holder is that the flexible strap 1001 allows polishing of threads in confined areas where other tools may not fit. FIG. 10C shows an alternative embodiment of the flexible stone holder, comprising closed cutouts 1011 disposed within the end portions 1002 and 1006. During use, a user can securely grip the strap 1001 by placing his fingers through closed cutouts 1011.

FIGS. 11A and 11B show the use of flexible polishing stone holder 1000. FIG. 11A is a front view of a bolt 1102 being polished by flexible polishing stone holder 1000. To polish the bolt 1102, the flexible polishing stone holder 1000 is moved back and forth in the direction indicated by arrow D. FIG. 11B is a side view, showing flexible polishing stone holder 1000 placed around threaded portion 1103 of bolt 1102. The flexible polishing stone holder 1000 is moved back and forth in direction D by pulling on each end of the flexible polishing stone holder 1000 in an alternating manner.

Figure 12A:
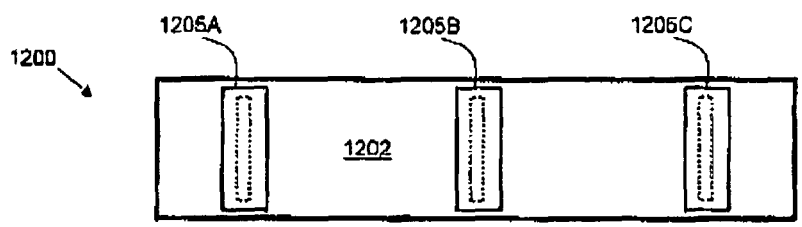
FIGS. 12-14 show additional alternative embodiments of the present invention.
Figure 12B:
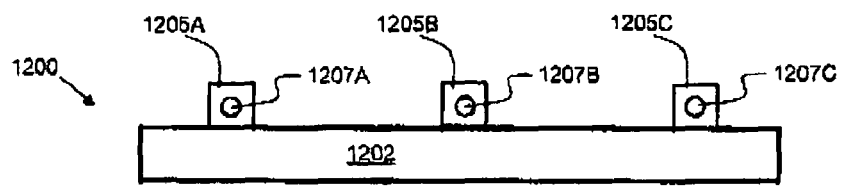
Figure 12C:
Figure 13:
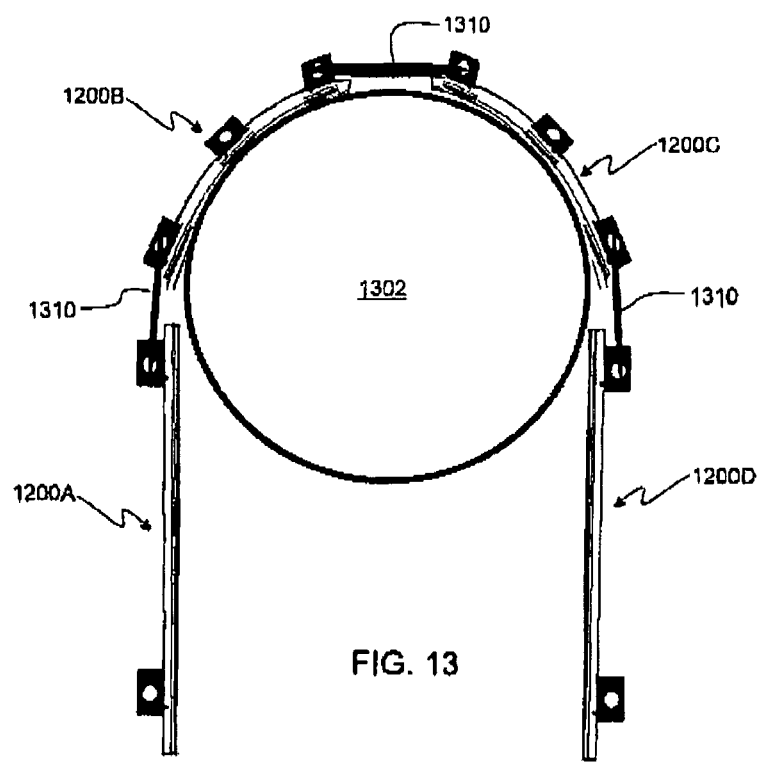
Figure 14:
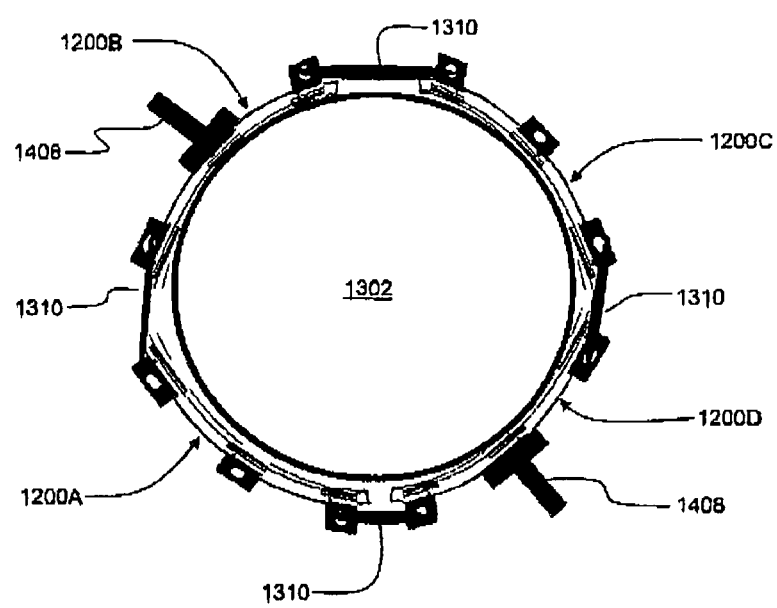

FIGS. 12-14 show additional alternative embodiments of the present invention. FIG. 12A shows a top view (outer surface) of a polishing stone holder 1200. Polishing stone holder 1200 comprises urethane strap 1202, and a plurality of lugs, indicated as 1205A, 1205 B, and 1205C. FIG. 12B is a side view of polishing stone holder 1200, showing the lugs 1205A-1205C, and corresponding holes for each lug 1207A-1207C. FIG. 12C shows a bottom view (inner surface) of polishing stone holder 1200. The holes 1207 traverse the lugs 1205 such that additional apparatuses may be attached to the lugs 1205, as will be described in upcoming figures.

Polishing stone 1210 is preferably cast as part of strap 1202, with the thread pattern as part of a mold (not shown) used to form the strap 1202. Preferably, polishing stone 1210 is larger than that of the embodiment shown in FIG. 10A, and occupies most of the available space on strap 1202.

FIG. 13 shows an example usage of a plurality of polishing stone holders similar to polishing stone holder 1200. In FIG. 13, a plurality of polishing stone holders 1200A-1200D are used to inspect a large-diameter threaded shaft 1302. In practice, such a shaft may exceed 18 inches in diameter. A propeller shaft of an ocean-going ship is one example where such large threaded shafts may be found. The polishing stone holders 1200A-1200D are linked together via connector bands 1310. Connector bands 1310 are preferably elastic and engage hole (e.g. 1207A of FIG. 12B) of lugs (e.g. 1205A of FIG. 12B) of neighboring polishing stone holders. In one embodiment, the connector bands are adjustable in length to accommodate various sizes of threaded shafts. To inspect the shaft 1302, an up-and-down "shoeshine" motion is used by pulling on the opposite end polishing stone holders 1200A and 1200D in a reciprocal manner.

FIG. 14 shows an example usage of a plurality of polishing stone holders similar to polishing stone holder 1200. In FIG. 14, a plurality of polishing stone holders 1200A-1200D are formed in a closed loop via connector bands 1310. A plurality of handles 1408 are attached to the center lugs (e.g. 1205B of FIG. 12B) of one or more polishing stone holders 1200A-1200D. The handles are then moved by the user to pass the polishing stone holders 1200A-1200D over the threads of shaft 1302.

Figure 14B:
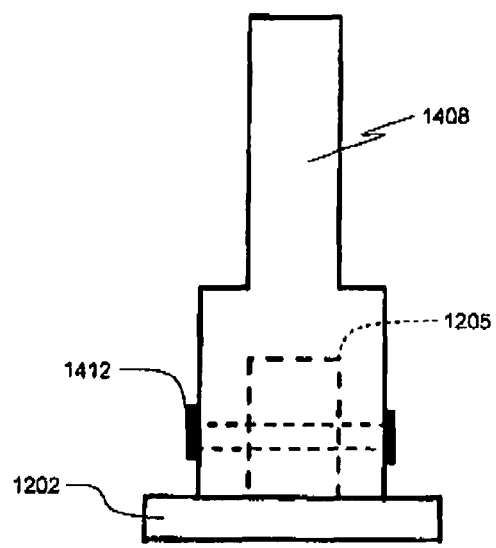

FIG. 14B shows detail of an exemplary embodiment of handle 1408 mounted to a lug 1205. The lug 1205 is integral to strap 1202, and a fastener 1412 traverses the handle 1408 and lug 1205 to secure the handle 1408 to the lug 1205, and hence to a polishing stone holder. Fastener 1412 may comprises a threaded fastener, a friction-fit fastener, or any other suitable fastening mechanism to secure handle 1408 to lug 1205. The use of the handles 1408 as shown in FIG. 14 may be convenient in situations where there is not sufficient clearance to use the "open loop" configuration depicted in FIG. 13.

As can now be appreciated, embodiments of the present invention provide an improved method and apparatus for inspecting and repairing threads on large bolts and threaded holes. Although the description above contains many specific details, these should not be construed as limiting the scope of the invention, but merely as providing illustrations of some of the presently preferred embodiments of the present invention. The present invention may have various other embodiments. Furthermore, while the form of the invention herein shown and described constitutes a preferred embodiment of the invention, it is not intended to illustrate all possible forms thereof. It will also be understood that the words used are words of description rather than limitation, and that various changes may be made without departing from the spirit and scope of the invention disclosed. Thus, the scope of the invention should be determined by the appended claims and their legal equivalents, rather than solely by the examples given.

What is claimed is:

1. A polishing device for polishing threads of a bolt, the device comprising:
    a flexible strap that is configured and disposed to wrap around at least a portion of the bolt, the flexible strap comprising a middle polishing portion and two end portions devoid of polishing material, and wherein the two end portions are of a different shape than the middle portion, thereby enabling a user to securely grip the flexible strap; and
    an abrasive polishing element disposed on the middle portion of the flexible strap, the polishing element including a polishing thread profile having a spacing factor of at least two (2).

2. The device of claim 1, wherein the polishing element includes urethane mixed with metal oxide.

3. The device of claim 1, wherein the spacing factor is two (2).

4. The device of claim 1, wherein the flexible strap includes a plurality of cutout areas disposed within the end portions.

5. The device of claim 1, wherein a width of the flexible strap is in the range of two inches to four inches (2"-4"), and wherein a length of the flexible strap is in the range of eight inches to ten inches (8"-10").

6. The device of claim 1, further comprising a plurality of lugs disposed on a side of the flexible strap opposite the abrasive polishing element.

7. The device of claim 6, wherein each one of the plurality of lugs includes a hole that traverses the lug.

8. The device of claim 7, further comprising at least one connecting band configured to fasten the polishing device to a second polishing device.

9. The device of claim 7, further comprising at least one handle, the at least one handle configured and disposed to attach to at least one of the plurality of lugs on the flexible strap.

10. The device of claim 1, wherein the flexible strap and the abrasive polishing element are constructed of a single piece of cast urethane material.

11. The device of claim 1, wherein the flexible strap is constructed of a material selected from the group consisting of rubber, canvas and another sturdy textile.

12. The device of claim 1, wherein the abrasive polishing element is secured to the flexible strap by a hook-and-loop fastener.

13. The device of claim 1, wherein the abrasive polishing element is secured to the flexible strap by snaps.

* * * * *